(12) United States Patent
Fox et al.

(10) Patent No.: US 11,488,689 B2
(45) Date of Patent: Nov. 1, 2022

(54) PREDICTION MODELING SYSTEM FOR CLINICAL TRIALS

(71) Applicant: Icon Clinical Research Limited, Dublin (IR)

(72) Inventors: Ronan Fox, Dublin (IR); Sean Kelly, Dublin (IR); Thomas O'Leary, Dublin (IR)

(73) Assignee: Icon Clinical Research Limited, Dublin (IE)

(*) Notice: Subject to any disclaimer, the term of this patent is extended or adjusted under 35 U.S.C. 154(b) by 331 days.

(21) Appl. No.: 16/041,332

(22) Filed: Jul. 20, 2018

(65) Prior Publication Data
US 2019/0131001 A1    May 2, 2019

(30) Foreign Application Priority Data
Nov. 1, 2017  (EP) .................................... 17199577

(51) Int. Cl.
*G16H 10/20* (2018.01)
*G16H 50/50* (2018.01)
(Continued)

(52) U.S. Cl.
CPC ............. *G16H 10/20* (2018.01); *G06Q 10/04* (2013.01); *G06Q 10/063* (2013.01);
(Continued)

(58) Field of Classification Search
None
See application file for complete search history.

(56) References Cited

U.S. PATENT DOCUMENTS

2006/0184493 A1*  8/2006  Shiftman ............... G06Q 90/00
                                                             706/47
2016/0357944 A1*  12/2016  Iyer ........................ G06F 19/00
(Continued)

FOREIGN PATENT DOCUMENTS

WO    WO 2015/138338 A1    9/2015
WO    WO-2015134390 A1 *  9/2015  ............. A61B 5/082

OTHER PUBLICATIONS

S. Lindblad, S. Ernestam, A.D. Van Citters, C. Lind, T.S. Morgan, E.C. Nelson, Creating a culture of health: evolving healthcare systems and patient engagement, QJM: An International Journal of Medicine, vol. 110, Issue 3, Mar. 2017, pp. 125-129. (Year: 2017).*

*Primary Examiner* — Lena Najarian
(74) *Attorney, Agent, or Firm* — Bookoff McAndrews, PLLC (57) ABSTRACT

Servers of a clinical trial support network have digital data processors which execute an automated tracking and prediction model for patient engagement. The model is linked with an interfacing tool used by doctor managing a group of patients and an interfacing tool used by patients for real time capture of events. The system processes factor values to generate and track in real time a patient engagement index. The system uses the factor values to maintain a taxonomy of factor values. The system is also programmed to determine values of characteristics derived from the factors, such as a characteristic indicating time-based trend of a factor. Another advantageous characteristic is impact of multiple occurrences of a factor.

18 Claims, 3 Drawing Sheets

(51) Int. Cl.
*G16H 50/30* (2018.01)
*G06Q 10/06* (2012.01)
*G06Q 10/04* (2012.01)
G16H 50/20 (2018.01)
G16H 10/60 (2018.01)
G16H 50/70 (2018.01)

(52) U.S. Cl.
CPC ....... *G06Q 10/067* (2013.01); *G06Q 10/0631* (2013.01); *G16H 50/30* (2018.01); *G16H 50/50* (2018.01); *G16H 10/60* (2018.01); G16H 50/20 (2018.01); G16H 50/70 (2018.01)

(56) References Cited

U.S. PATENT DOCUMENTS

2017/0053102 A1  2/2017  Katz
2017/0154166 A1  6/2017  Klein et al.

* cited by examiner

Fig.5

PREDICTION MODELING SYSTEM FOR CLINICAL TRIALS

CROSS-REFERENCE TO RELATED APPLICATIONS

This patent application claims the benefit under 35 U.S.C. § 119 to European Patent Application No. EP17199577.2, filed on Nov. 1, 2017, the entirety of which is incorporated herein by reference.

INTRODUCTION

The current disclosure relates to management of clinical trials.

Clinical trials require very difficult and comprehensive management processes, both for clinical reasons and also for managing engagement of the participating patients. Even where there is excellent management in the clinical aspects trials may not be successful because of failure of significant numbers of patients to remain engaged.

The disclosure is directed towards providing enhanced automation to address this problem.

WO2015/138338 (TCN Technologies) describes a clinical trial patient engagement tool which provides information such as pre-enrolment content to portable devices.

SUMMARY OF THE INVENTION

We describe an embodiment of an automated prediction modeling method implemented by a clinical trial network, the method being performed by a plurality of digital data processors and comprising the steps of:
- interfacing with a patient or clinical trial server to capture patient engagement events and determining associated factor values,
- processing said factor values to generate and track in real time a patient engagement index during the course of a trial, and
- generating notifications according to said patient engagement index.

In one embodiment, the interfacing is with a tool used by a doctor managing a group of patients, in which the doctor identifies him/herself through an authentication process and the patient under consideration through a mechanism such as a search field, or with an interfacing tool used by patients.

The network may maintain a taxonomy of factor values in order to provide suggested values during the configuration phase of future clinical trials where the PEI is to be calculated. In one embodiment, the processors automatically record a pattern of events of historical clinical trials leading to patient disengagement, and use said record to dynamically update weightings applied to factor values.

In one embodiment, the processors associate factor values with attributes of a clinical trial to quantify the impact on the PEI of attributes.

The attributes may include one or more selected from therapeutic area, patient age profile, geographic location, gender, and geographic distribution of clinical trial sites.

In one embodiment, the attributes are compared to enhance historical PEI analysis and make confidence intervals more accurate using larger sample sizes, and in which clinical trials are associated based on a threshold comparator values, determining which PEIs from specific trials are to be included according to the following formula:

$$\text{similarity}(x, y) = \sum_{i=1}^{n} w(i) * \text{attribute}(y_i) \bigg/ \sum_{i=1}^{n} w(i) * \text{attribute}(x_i)$$

in which,
- similarity (x,y) is a function measuring the similarity of studies x and y
- n is the number of attributes,
- w(i) is the weighting associated with attribute i
- attribute ($y_i$) is attribute I associated with study y and
- attribute ($x_i$) is attribute I associated with study x.

The processors may determine values of characteristics derived from the factors, such as a behaviour characteristic indicating time-based trend of a factor, or impact of multiple occurrences of a factor. In one embodiment, the network processor applies different weightings to factors.

The network may analyse historical outcomes for patient engagement to modify weightings. The network may apply different weightings according to time within a clinical trial.

The network may track a value of slope of one or more factors, and to generate an alert according to the slope. Preferably, the factors are represented in a database which allows persistence of data linked with the factors.

The network may link persistent data includes one or more selected from associated event type, importance associated with the event type, and data to ensure that the total of all the weightings applied to all factors is normalized.

In one embodiment, the processors monitor a differential characteristic for slope of the patient engagement index, which is calculated as:

$$\frac{dy_i}{dx_i} = (y_{i+1} - y_{i-1}) / (x_{i+1} - x_{x-1})$$

where $y_i$ is the PEI for a time period I,
and xi is the current time period.

One embodiment includes a clinical trial network comprising a plurality of digital data processors, at least one database, and communication interfaces, the processors being configured for performing an automated prediction modeling method comprising the steps of:
- interfacing with a patient or clinical trial server to capture patient engagement events and determining associated factor values,
- processing said factor values to generate and track in real time a patient engagement index during the course of a trial, and
- generating notifications according to said patient engagement index.

The network processors may be configured to perform any of the other method operations set out above.

The following disclosure provides a non-transitory computer storage medium comprising software code for performing steps of a method of any embodiment when executed by digital data processors.

Detailed Description of the Invention

BRIEF DESCRIPTION OF THE DRAWINGS

The disclosed embodiments will be more clearly understood from the following description of some embodiments thereof, given by way of example only with reference to the accompanying drawings in which.

DESCRIPTION OF THE EMBODIMENTS

Figure 1:
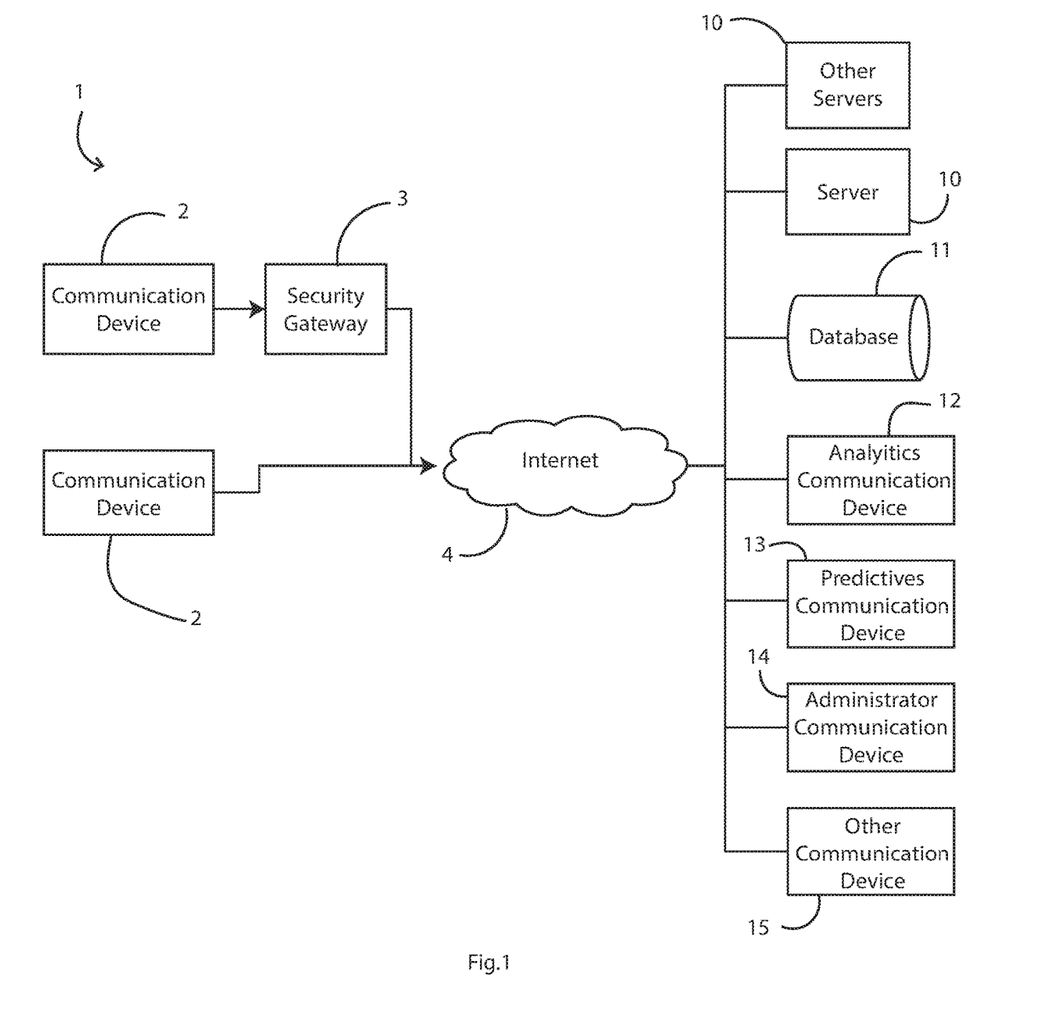
FIG. 1 is a diagram illustrating a clinical trial network including the main hardware components, according to one or more embodiments.

Referring to FIG. 1 a clinical trial support network 1 comprises communication devices 2 linked by a security gateway 3 to the Internet 4. This in turn links the devices 2 with servers 10, a database 11, an analytics communication device 12, a predictive communication device 13, an administrator communication device 14, and with other communication devices 15. Each device and server comprises digital data processors and communication interfaces as is well known in the art. The database software comprises a document store or a relational database management system which supports a schema required to hold data relating to patient engagement indexes, but not limited to:

The configuration of the software including base factors and weightings

Patient event data including the type of event, the date and time associated with the event and other metadata that may be generated either manually or automatically as part of the processing and creation of the patient engagement index Patient engagement indexes (PEIs) calculated Any aggregations of the patient engagement index allowing an ability to dimension the data by the contributory factors, ranking of importance of factors across the patient data set under consideration. The dimensions can be used individually or in combination with the following individual examples:

Contributing Factor—showing the impact of the data set of individual factors on Patient Engagement Indexes, and allowing a comparison of those factors to identify those with the highest impact so that they can be used as indicative factors in the future where they occur.

Patient Attributes including demographic data, geographic data, disease or condition, inclusion score, and site can be used individually or combined together and with other dimensions to establish relationships between attributes and the Patient Engagement Indexes.

Study Attributes including the drug, disease, inclusion/exclusion criteria.

Any audit trails and logs required to aid in the regeneration or review of indexes created, factors influencing the events influencing the indexes.

The servers are configured in hardware terms according to the specified requirements in the clinical trial network. In one example the servers have a speed in the range of 2 to 3 GHz, have in the range of 4 to 16 cores, and a memory capacity of 12 to 15 GB. However, the parameters may be different, depending on the capacity requirements.

The communication devices 2 and the servers 10 to 15 are used by the patient and by clinical trial staff at the site, and the clinical research organisation. On the server side of the topology, the servers 10 to 15 include servers to model, manage, analyse, and predict the interactions between the patient and the study team (whether that study team is physical, remote, or virtual). Those devices on the server side continually interface with the database 11 of patient/trial interactions and apply algorithms to provide trends and predictions as to the likely next step of the patient in the trial (leave or stay). The database technology may be instantiated as an RDBMS or as an in-memory data grid spanning clusters of servers to allow for faster throughput and real time processing of events as they occur during the execution of the clinical trial. The deployment of the database server may be in a private data centre on in a secured public cloud infrastructure to allow for quick scale up during periods of intense activity in a clinical trial and where the volumes of events approach that of a data stream and will require additional infrastructure to support spikes in demand during these periods.

At least one of the servers of the network has digital data processors which execute an automated tracking and prediction model for patient engagement. The processors may be spun up as required and determined by the scale needs of the network and the volume of events incoming to the system. This could be enabled through a micro services architecture which will utilize self-healing and annealing infrastructures, deploying new instances as detected by management software (where services drop offline or where the incoming traffic is too much for the existing number of services deployed). The model is linked with the following for real time capture of events:

interfacing tool used by the doctor managing a group of patients, where the doctor identifies him/herself through a logging on process and the patient under consideration through a mechanism such as a search field, or through some selection mechanism interfacing tool used by patients.

The prediction modeling system digital data processors process factor values to generate and track in real time a patient engagement index (PEI). They use the predictions generated over time to aid in defining factors for future trials. For example, if the series of factors in a number of trials which shared similar attributes resulted in an early exit then those factors could be used as a taxonomy of factors inputting into other new trials with those similar attributes. This taxonomy is in one example a list of factors and the aggregated or average importance relating to each factor and can be used as input to the configuration step of future trials where the values can either be used as suggested by the system, or used as suggestions where the user can chose to override based on other to be determined variables.

The factors are represented in the system in the database 11 which will allow the persistence of data such as:

The Event Type

The importance associated with the event type (which may be represented as a number between 0 and 1 (the higher the number the greater the impact)

Data to ensure that the total of all the weightings applied to all factors is normalized (or that they cannot exceed the sum of 1)

The system is also programmed to determine values of characteristics derived from the factors, such as a characteristic indicating time-based trend of a factor. Another advantageous characteristic is impact of multiple occurrences of a factor.

In more detail, the prediction modeling system enumerates factors that could influence a patient's engagement with a trial, and it can be customized and extended during the design of a trial to reflect the nature of the trial and the factors influencing patients. The system identifies and models factors for key milestone events such as patients being borderline on trial inclusion during eligibility determination, study duration, and the demographic of the patient cohort where patients may split their domicile with associated drop out/non-compliance rates, and meeting events.

Factors are derived from data arising from meeting events, including:
Patient On Time
Patient No Show
Patient Cancelled
Patient Disinterested
Patient Unsure
Patient Accompanied
Patient Ease of Access to meeting place
Patient Sentiment Some of these are internal to the trial and others are external and impossible to change directly, but each has an influence on the patient's participation. This data can be captured by the study team member that meets the patient, or could be filled out by the patient through a questionnaire.

The prediction modeling system captures these, and incorporates them into an algorithm which estimates the level of patient engagement.

Combining Factors

The model generates and maintains a taxonomy of factors and computes characteristics associated with the factors, as follows:

| Characteristic | Description |
|---|---|
| Slope/Behaviour Influence | A formula that describes the time-based impact of the factor. This could be a straight line approximation or a more complex and potentially accurate formula |
| Maximum Value | The maximum value associated with the factor (default 1) |
| Minimum Value | The minimum value associated with the factor (default 0) |
| Repeat Effect Influence | The impact of multiple occurrences of this factor throughout the various phases of the patient interaction to date. This is either as simple as a multiplier or divisor or could use a formula incorporating phases, frequency, event types and so on |

Graphing Patient Engagement

As an example consider a set of two factors (On Time and Interest) contributing to a Patient Engagement Index (PEI) score for a fictitious patient engagement score over a period of 12 months of a clinical trial:

| Time (Months) | PEI | On Time Factor | Interest Factor | Base On Time Factor | On Time − Patient | Base Interest Factor | Patient Interest |
|---|---|---|---|---|---|---|---|
| M1 | 0.32 | 0.00 | 0.63 | 0.70 | 0.00 | 0.90 | 0.70 |
| M2 | 0.63 | 0.65 | 0.62 | 0.65 | 1.00 | 0.87 | 0.71 |
| M3 | 0.52 | 0.42 | 0.62 | 0.60 | 1.00 | 0.84 | 0.72 |
| M4 | 0.48 | 0.36 | 0.61 | 0.55 | 0.00 | 0.81 | 0.73 |
| M5 | 0.43 | 0.26 | 0.60 | 0.50 | 0.00 | 0.78 | 0.74 |
| M6 | 0.47 | 0.35 | 0.59 | 0.45 | 1.00 | 0.75 | 0.75 |
| M7 | 0.46 | 0.34 | 0.59 | 0.40 | 1.00 | 0.77 | 0.76 |
| M8 | 0.41 | 0.23 | 0.60 | 0.35 | 0.00 | 0.79 | 0.77 |
| M9 | 0.40 | 0.19 | 0.61 | 0.30 | 0.00 | 0.81 | 0.78 |
| M10 | 0.38 | 0.14 | 0.62 | 0.25 | 0.00 | 0.83 | 0.79 |
| M11 | 0.41 | 0.18 | 0.64 | 0.20 | 1.00 | 0.85 | 0.80 |
| M12 | 0.40 | 0.16 | 0.65 | 0.15 | 1.00 | 0.87 | 0.81 |

The range of values for the factors above are in the range of −1, to +1, indicating a positive or negative impact on the PEI. However, the PEI would retain a range of (0, 1).

The Base Factors have differing impact as the trial progresses. For example, in one trial the trial design has indicated that the patient being on time has a significant impact early on in the trial but less so as the trial proceeds (perhaps being late for appointments early on in the trial is more significant that later on). The Base Patient Interest was defined as being very impactful at all stages of the trial, but particularly at the start and the end periods.

The factor calculations in this example are simple formulae:

$$\text{factor}(x) = \left( \text{baseFactor}(x) * \text{patientFactor}(x) + \left( \sum_{n=x-4}^{n=x-1} \text{baseFactor}(n) * \text{patientFactor}(n) / (n-x) \right) \right) / 2$$

where x is the current time period and n is one of the preceding time periods.

So, for Month 1 the Interest Factor is the Base Interest Factor (0.9) multiplied by the Interest Displayed by the Patient (0.5) smoothed out by the average of that factor and the factor calculations from the previous months.

The Patient Engagement Index is given by the formula below (an average of the factors calculated above):

$$PEI(x) = \sum_{i=1}^{i=n} \text{factor}(i) / n$$

Where x is the time period, i is an instance of a factor for that month period and n is the total number of factors being considered as input for this Patient Engagement Index on this clinical trial.

Figure 2:
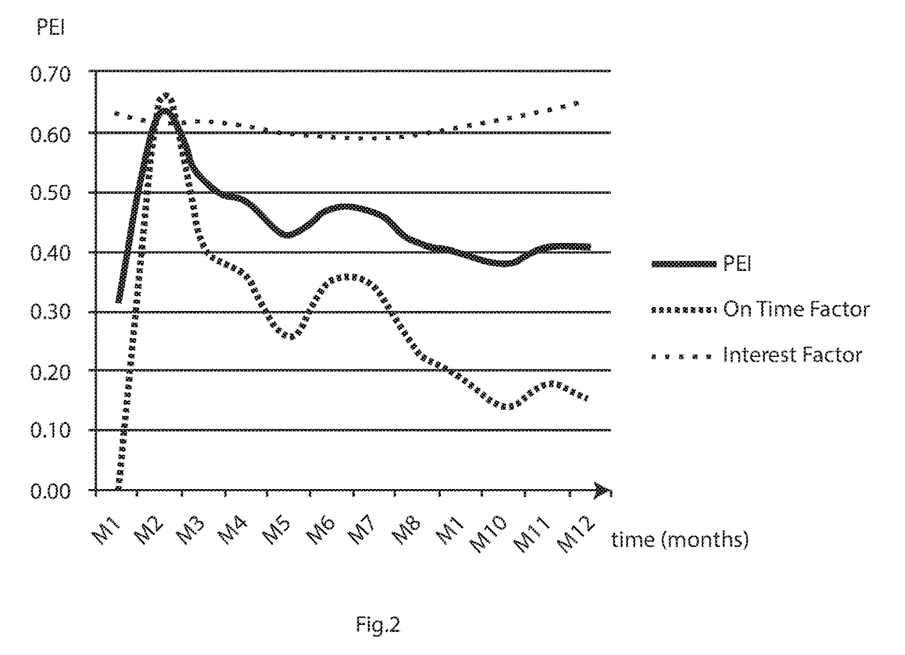
FIG. 2 is a plot generated by a prediction model of the network, indicating patient engagement factors tracked over time according to one or more embodiments.

Using the example calculations above a PEI chart as shown in FIG. 2 is generated.

Base Factors, Estimations through Learning

The base factors in FIG. 2 are "seed" entries initially entered during the clinical trial design.

Figure 3:
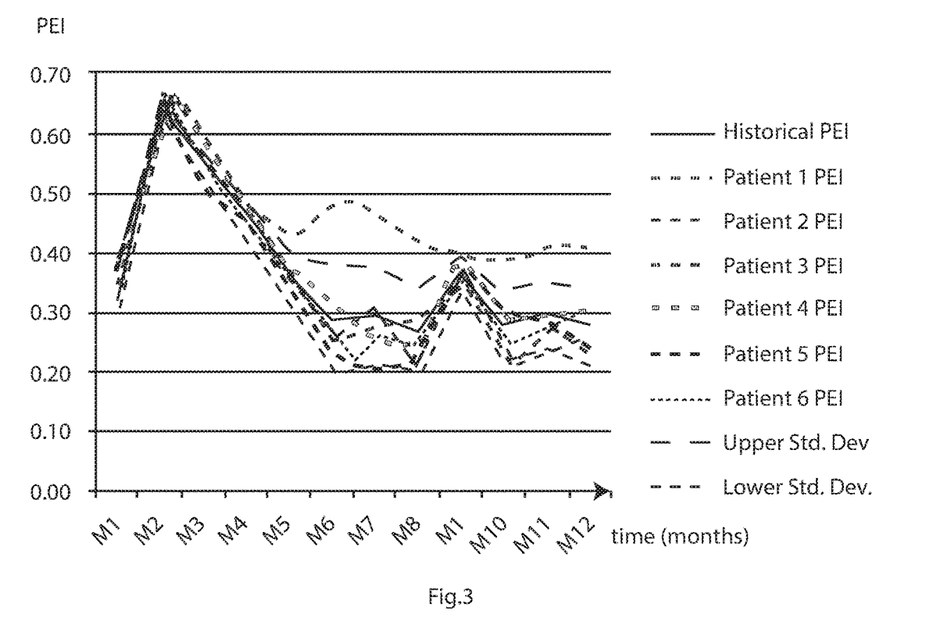
FIG. 3 is a plot showing factors over time for multiple patients according to one or more embodiments.

Aggregated analysis of historical PEI across all patients in a study, or across a series of studies provides indicators of the impacts of various factors at various time points in the clinical trial. FIG. 3 illustrates by the continuous line the average of all PEIs for a selection of 6 patients. This could also be done for the various patient factors to establish the historical impact of those factors on the PEI. The system uses historical evidence leading up to a PEI for a cross section of patients indicating the events that led up to the patient leaving a trial (where the PEI went to 0).

To further understand the subtleties of various factors and their impact on the PEI the system uses attribute-based matching of PEI values and trends across groups of similar studies. For example, it can use attributes such as:

| Attribute | Weighting |
|---|---|
| Therapeutic area | .3 |
| Patient age profile | .3 |
| Geographic location | .1 |
| Gender | .2 |
| Geographic distribution of sites | .1 |

These attributes are compared allowing additional input into the Historical PEI above and can further make the confidence intervals more accurate using larger sample sizes (as shown in FIG. 3). Studies are included based on a threshold "comparator value" given by the trial designer above, determining which PEIs from specific studies would be included given the following formula:

$$\text{similarity}(x, y) = \sum_{i=1}^{n} w(i) * \text{attribute}(y_i) \Big/ \sum_{i=1}^{n} w(i) * \text{attribute}(x_i)$$

where similarity (x,y) is a function measuring the similarity of studies x and y n is the number of attributes w(i) is the weighting associated with attribute i attribute ($y_i$) is attribute I associated with study y and attribute ($x_i$) is attribute I associated with study x As similarity (x,y)→1 this implies two studies are similar for the purposes of the PEI. A study designer would then choose a threshold over which studies could be included in the analysis.

Part of the analysis is to determine which base factors are consistently having an impact on PEIs in specific types of studies, allowing the system to better predict patient engagement and perhaps define interventions intended to improve engagement and thus patient retention rates before the patient exits within a PEI of 0.

To identify the base factors driving a PEI towards 0 (below 0.1), if the PEI and contributing factor data is held in an RDBMS then the SQL to identify negatively contributing factors might be for a specific patient:

Select * from contributions where value<PEI and PEI<0.1;

Understanding and Predicting Trends

A trend in the PEI can be determined by calculating an average differential over the data as follows:

| Month | PEI | Differential |
|---|---|---|
| 1 | 0.32 | |
| 2 | 0.63 | 0.101042 |
| 3 | 0.52 | −0.07583 |
| 4 | 0.48 | −0.0439 |
| 5 | 0.43 | −0.00481 |
| 6 | 0.47 | 0.017766 |
| 7 | 0.46 | −0.02936 |
| 8 | 0.41 | −0.03332 |
| 9 | 0.40 | −0.01694 |
| 10 | 0.38 | 0.00393 |
| 11 | 0.41 | 0.012246 |
| 12 | 0.40 | 0.036914 |

The Differential is calculated as:

$$\frac{dy_i}{dx_i} = (y_{i+1} - y_{i-1}) / (x_{i+1} - x_{x-1})$$

where $y_i$ is the PEI for month i and xi is the current month

Figure 4:
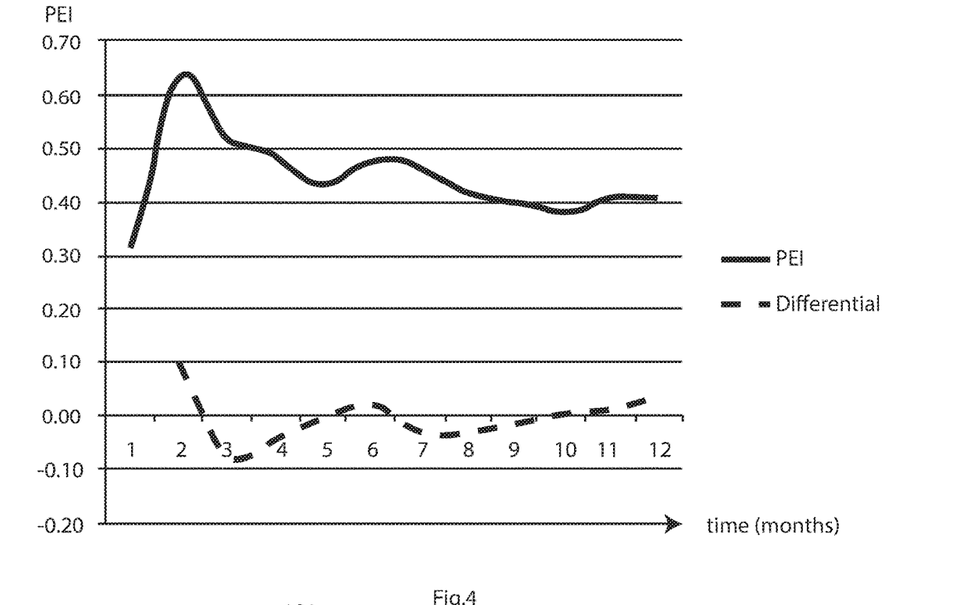
FIG. 4 is a plot of a derived parameter, generated by the prediction model according to one or more embodiments.

The resultant chart is shown in FIG. 4. Each time the Differential goes below 0 this indicates a downward trend in the PEI.

Figure 5:
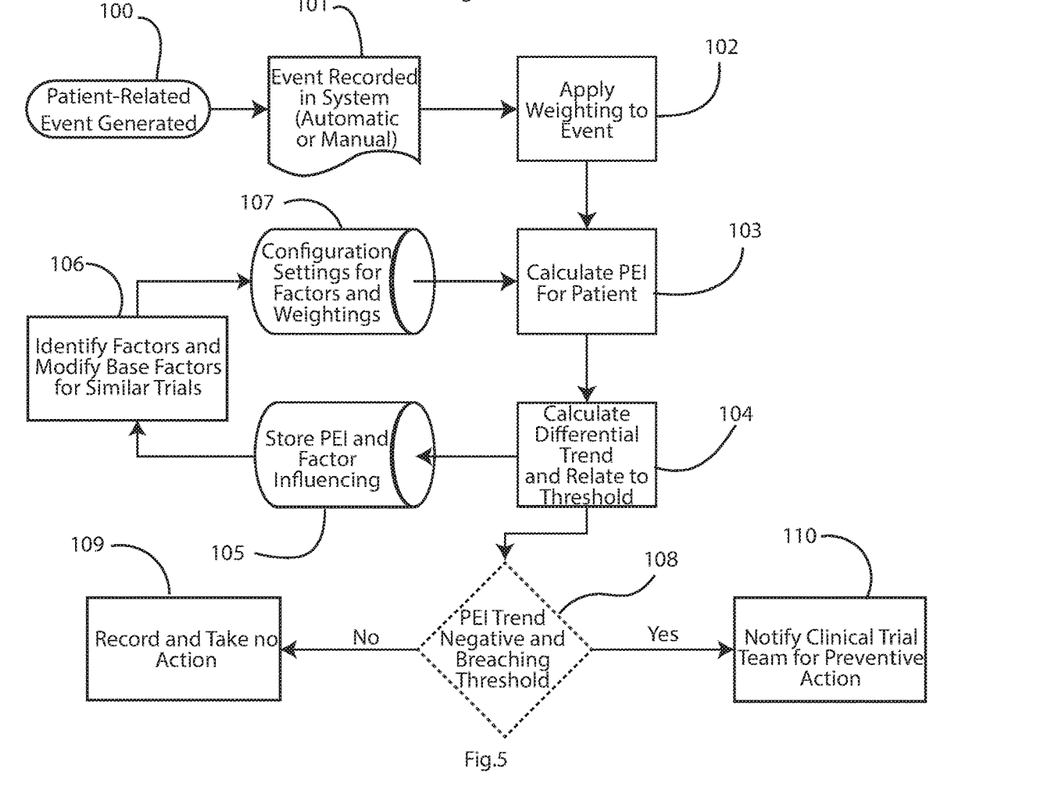
FIG. 5 is a workflow diagram for a process used in creating and updating a patient engagement index and contributory factors, according to one or more embodiments.

Referring to FIG. 5 the steps performed by digital data processors may be summarized as follows:

100, A patient-related event is generated, being associated with a base factor.

101, The event is recorded in the system in a persistent database.

102, A weighting is applied to the event.

103, A current PEI for the patient is updated, or is initially generated if it is the first event for the patient. This involves use of configuration settings for factors and weightings.

104, A differential trend is calculated, and it is related to a threshold.

105, 106, 107, the PEI is stored with the currently influencing factor. The PEI changes and the factors influencing the changes also are identified and base factors are modified for future similar trials. These impacts are stored for use in future trials (and PEI generation) so that initial values can be suggested to users as they configure future PEI generation algorithms for future (or indeed the current) trial.

108, A decision process in which the PEI trend is measured relative to prior values and where the PEI is also compared to the threshold. If both are true, then the Clinical Trial Team is notified (110) and appropriate action is taken. Otherwise the trend value is noted (109) and no action is taken.

The PEI can also be tracked to evaluate the patient experience in a trial and used to determine how to develop more patient centric trials and thus more successful trials with higher patient retention and engagement rates.

The PEI can also be tracked and addressed through the different Trial phases (2 through 4) and practices refined accordingly for better outcome in the more extensive later stages of drug trials. Phase 2 starting with seed data and phases 3 and 4 refining impact analysis through machine learning.

The prediction tool provides early stage indicators of the following:

Factors contributing to early patient exits from trials

Identifying retention strategies based on those factors

Learning across trials to proactively develop retention strategies

Ideal patient identification based on cohorts that typically stay on a trial

Spending effort and resources more efficiently by identifying strategies in early stages that can be applied to later more expensive phases of trials for a specific therapy It will be appreciated that the disclosed embodiment(s) provides an automated model and data processing algorithm for identifying most likely future events and for enabling identification of remedial actions to be performed by study staff to maximize the chance of a patient remaining on a clinical trial.

This model can be applied in a single stage or over all trial phases.

A patient interacting with a clinical trial as part of a Patient Journey can be modeled as a series of events—each of which has a limited number of outcomes with an associated impact on the next potential event that the patient will enact.

The model maximizes the value of a Patient Engagement Index (PEI) associated with keeping a patient on a trial, the PEI having a range of PEI=0, patient has left the trial PEI=1, patient is fully engaged on the trial At any point in time, while the patient is on the trial, the PEI will fluctuate between 0 and 1.

It will be appreciated that the disclosure relates to the experience of a patient on a specific clinical trial and provides mechanisms to model and predict the behaviour of the patient on that clinical trial so that their premature exit can be predicted and in some cases steps taken to lessen the risk of that exit The disclosure is not limited to the embodiments described but may be varied in construction and detail.

The invention claimed is:

1. An automated prediction modeling method for a clinical trial network, the method being performed by a plurality of digital data processors and comprising the steps of:
   at one or more servers implementing the clinical trial network, monitoring a data connection between one or more interfacing tools and the one or more servers for incoming event data associated with a trial; and
   for each instance of incoming event data, using a quantity of the plurality of digital data processors based on one or more of a monitored load on the clinical trial network or a monitored volume of the incoming event data to perform operations, including:
      capturing the instance of event data, the instance of event data associated with an interaction between a patient, via one of the one or more interfacing tools, and one of the one or more servers, the interaction corresponding to a current time period of the trial;
      accessing a taxonomy of factors associated with patient engagement with the trial, the taxonomy including base factor values for each of the factors at various time periods of the trial, the base factor values associated with a predicted impact of each of the factors at the various time periods of the trial;
      generating a patient engagement event based on the instance of event data;
      determining, based on the generated patient engagement event, patient factor values corresponding to the current time period of the trial;
      determining factor values for the factors in the taxonomy, based on the base factor values at the current time period of the trial, and on the patient factor values corresponding to the current time period of the trial;
      generating a patient engagement index (PEI) corresponding to the current time period of the trial, based on the determined factor values;
      accessing data that includes at least one PEI corresponding to one or more previous time periods of the trial;
      determining a slope of the PEI based on the PEI corresponding to the current time period of the trial and the at least one PEI corresponding to the one or more previous time periods of the trial;
      predicting a behavior of the patient for a subsequent time period of the trial, based on the determined slope; and
      generating and transmitting a notification based on the predicted behavior of the patient.

2. The prediction modeling method as claimed in claim 1, wherein the one of the one or more interfacing tools is either (i) a tool used by a doctor managing a group of patients, in which the doctor identifies him/herself through an authentication process and the patient under consideration through a search field, or (ii) an interfacing tool used by the patient.

3. The prediction modeling method as claimed in claim 1, wherein the operations further include:
   accessing weightings for the factors, the weightings based on a pattern of events of historical clinical trials leading to patient disengagement; and
   applying the weightings to the factor values prior to generating the PEI.

4. The prediction modeling method as claimed in claim 1, wherein the quantity of processors are further configured to associate the factor values with attributes of clinical trials to quantify an impact of the attributes on the PEI.

5. The prediction modeling method as claimed in claim 4, wherein the attributes include one or more selected from therapeutic area, patient age profile, geographic location, gender, and geographic distribution of clinical trial sites.

6. The prediction modeling method as claimed in claim 4, wherein:
   the base factor values are based on one or more historical clinical trials; and
   specific trials are included in the one or more historical trials based on whether a similarity between the trial and the specific trials is above a threshold value; and
   the similarity is determined according to the following formula:

$$\text{similarity}(x, y) = \sum_{i=1}^{n} w(i) * \text{attribute}(y_i) \Big/ \sum_{i=1}^{n} w(i) * \text{attribute}(x_i)$$

in which,
n is a number of the attributes,
w(i) is a weighting associated with attribute i
attribute (yi) is attribute I associated with trial y and
attribute (xi) is attribute I associated with trial x.

7. The prediction modeling method as claimed in claim 1, wherein the quantity of processors are further configured to determine values of characteristics derived from the factors.

8. The prediction modeling method as claimed in claim 7, wherein the characteristics include a behavior characteristic indicating time-based trend of a factor.

9. The prediction modeling method as claimed in claim 7, wherein the characteristics include an impact of multiple occurrences of a factor.

10. The prediction modeling method as claimed in claim 3, wherein the quantity of processors are further configured to analyse historical outcomes for patient engagement to modify the weightings.

11. The prediction modeling method as claimed in claim 3, wherein the quantity of processors are further configured to apply different weightings to the factors at different time periods within the trial.

12. The prediction modeling method as claimed in claim 1, wherein the quantity of processors are further configured to track a value of slope of one or more of the factors, and are configured to generate an alert according to the slope.

13. The prediction modeling method as claimed in claim 1, wherein the factors are represented in a database that includes data linked with the factors.

14. The prediction modeling method as claimed in claim 13, wherein linked data includes one or more selected from associated event type, importance associated with the event type, and data configured to cause weightings applied to all factors to be normalized.

15. The prediction modeling method as claimed in claim 1, wherein the quantity of processors are further configured to monitor a differential characteristic for the slope of the PEI, which is calculated as:

$$\frac{dy_i}{dx_i} = (y_{i+1} - y_{i-1})/(x_{i+1} - x_{x-1})$$

where yi is the PEI for a time period I, and xi is the current time period.

16. A clinical trial network comprising a plurality of digital data processors, one or more servers, and one or more interfacing tools, the plurality of digital data processors being configured for performing an automated prediction modeling method comprising the steps of:
  monitoring a data connection between the one or more interfacing tools and the one or more servers for incoming event data associated with a trial; and
  for each instance of incoming event data, using a quantity of the plurality of digital data processors based on one or more of a monitored load on the clinical trial network or a monitored volume of the incoming event data to perform operations, including:
    capturing the instance of event data, the instance of event data associated with an interaction between a patient, via one of the one or more interfacing tools, and one of the one or more servers, the interaction corresponding to a current time period of the trial;
    accessing a taxonomy of factors associated with patient engagement with the trial, the taxonomy including base factor values for each of the factors at various time periods of the trial, the base factor values associated with a predicted impact of each of the factors at the various time periods of the trial;
    generating a patient engagement event based on the instance of event data;
    determining, based on the generated patient engagement event, patient factor values corresponding to the current time period of the trial;
    determining factor values for the factors in the taxonomy, based on the base factor values at the current time period of the trial, and on the patient factor values corresponding to the current time period of the trial;
    generating a patient engagement index (PEI) corresponding to the current time period of the trial, based on the determined factor values;
    accessing data that includes at least one PEI corresponding to one or more previous time periods of the trial;
    determining a slope of the PEI based on the PEI corresponding to the current time period of the trial and the at least one PEI corresponding to the one or more previous time periods of the trial;
    predicting a behavior of the patient for a subsequent time period of the trial, based on the determined slope; and
    generating and transmitting a notification based on the predicted behavior of the patient.

17. A non-transitory computer storage medium comprising software code for performing steps of a method when executed by a plurality of processors, the method including:
  at one or more servers implementing a clinical trial network, monitoring a data connection between one or more interfacing tools and the one or more servers for incoming event data associated with a trial; and
  for each instance of incoming event data, using a quantity of the plurality of processors based on one or more of a monitored load on the clinical trial network or a monitored volume of the incoming event data to perform operations, including:
    capturing the instance of event data, the instance of event data associated with an interaction between a patient, via one of the one or more interfacing tools, and one of the one or more servers, the interaction corresponding to a current time period of the trial;
    accessing a taxonomy of factors associated with patient engagement with the trial, the taxonomy including base factor values for each of the factors at various time periods of the trial, the base factor values associated with a predicted impact of each of the factors at the various time periods of the trial;
    generating a patient engagement event based on the instance of event data;
    determining, based on the generated patient engagement event, patient factor values corresponding to the current time period of the trial;
    determining factor values for the factors in the taxonomy, based on the base factor values at the current time period of the trial, and on the patient factor values corresponding to the current time period of the trial;
    generating a patient engagement index (PEI) corresponding to the current time period of the trial, based on the determined factor values;
    accessing data that includes at least one PEI corresponding to one or more previous time periods of the trial;
    determining a slope of the PEI based on the PEI corresponding to the current time period of the trial and the at least one PEI corresponding to the one or more previous time periods of the trial;
    predicting a behavior of the patient for a subsequent time period of the trial, based on the determined slope; and
    generating and transmitting a notification based on the predicted behavior of the patient.

18. The prediction modeling method as claimed in claim 1, further comprising:
  modifying the base factor values based on the generated PEI.

* * * * *